United States Patent
Jin et al.

(10) Patent No.: US 11,724,120 B2
(45) Date of Patent: Aug. 15, 2023

(54) HIGH FREQUENCY MAGNETIC FOOT STIMULATION

(71) Applicant: Wave Neuroscience, Inc., Newport Beach, CA (US)

(72) Inventors: Yi Jin, Irvine, CA (US); James William Phillips, Fountain Valley, CA (US)

(73) Assignee: WAVE NEUROSCIENCE, INC., Newport Beach, CA (US)

( * ) Notice: Subject to any disclaimer, the term of this patent is extended or adjusted under 35 U.S.C. 154(b) by 0 days.

(21) Appl. No.: 16/903,772

(22) Filed: Jun. 17, 2020

(65) Prior Publication Data
US 2020/0384281 A1    Dec. 10, 2020

Related U.S. Application Data

(63) Continuation of application No. 15/295,537, filed on Oct. 17, 2016, now Pat. No. 10,716,951.

(51) Int. Cl.
*A61N 2/00* (2006.01)
*A61N 2/02* (2006.01)

(52) U.S. Cl.
CPC .............. *A61N 2/02* (2013.01); *A61N 2/006* (2013.01); *A61N 2/008* (2013.01)

(58) Field of Classification Search
CPC . A61N 2/00; A61N 2/02; A61N 2/004; A61N 2/006; A61N 2/008; A61N 2/12; A61N 2/002; A61N 2/06; A61M 21/02; A61H 2201/10; A61H 2201/164; A61H 2205/12; A61H 2205/125
See application file for complete search history.

(56) References Cited

U.S. PATENT DOCUMENTS

| | | | |
|---|---|---|---|
| 3,043,294 A * | 7/1962 | Neff | A61H 23/0218 601/61 |
| 4,492,221 A | 1/1985 | Kerley | |
| 5,084,003 A * | 1/1992 | Susie | A61H 23/0218 600/13 |
| 5,131,904 A * | 7/1992 | Markoll | A61N 2/02 600/14 |
| 5,501,682 A | 3/1996 | Edwards-Cofie | |
| 6,123,657 A * | 9/2000 | Ishikawa | A61N 2/12 600/9 |
| 6,301,506 B1 | 10/2001 | Den Boer et al. | |
| 7,520,849 B1 * | 4/2009 | Simon | A61N 2/02 600/14 |
| 8,897,868 B2 | 11/2014 | Mazar et al. | |
| 9,849,302 B1 * | 12/2017 | Fischell | A61N 2/008 |
| 10,716,951 B2 | 7/2020 | Jin et al. | |
| 2002/0056158 A1 | 5/2002 | Ferber et al. | |

(Continued)

FOREIGN PATENT DOCUMENTS

WO    2007044386 A2    4/2007
WO    2011011749 A1    1/2011

*Primary Examiner* — Kaylee R Wilson
(74) *Attorney, Agent, or Firm* — Buchalter

(57) ABSTRACT

High frequency repetitive magnetic pulses may be used to treat pain in the foot of a person by relaxing the muscle and reducing communication of pain signals by neurons in the treatment region. A device is disclosed, which is floor mounted and incorporates a cooling mechanism and heat sink to allow high frequency magnetic stimulation to the person's foot.

12 Claims, 6 Drawing Sheets

(56) References Cited

U.S. PATENT DOCUMENTS

| | | | |
|---|---|---|---|
| 2003/0023269 A1* | 1/2003 | den Boer | A61N 2/02 607/2 |
| 2003/0158585 A1 | 8/2003 | Burnett | |
| 2003/0171640 A1* | 9/2003 | Canedo | A61N 2/02 600/9 |
| 2004/0006289 A1* | 1/2004 | Liao | A61H 23/02 601/15 |
| 2004/0106843 A1* | 6/2004 | Ardizzone | A61N 2/12 600/9 |
| 2005/0148807 A1* | 7/2005 | Salkinder | A61N 2/06 600/9 |
| 2006/0241333 A1* | 10/2006 | Hunter | A61N 2/004 600/13 |
| 2007/0078292 A1* | 4/2007 | Markov | A61N 2/008 600/9 |
| 2007/0100392 A1 | 5/2007 | Maschino et al. | |
| 2007/0260291 A1* | 11/2007 | Hunter | A61N 1/00 607/50 |
| 2009/0243855 A1* | 10/2009 | Prokopuk | G01S 13/825 340/572.1 |
| 2010/0240972 A1* | 9/2010 | Neal | A61B 5/742 600/324 |
| 2011/0021863 A1* | 1/2011 | Burnett | A61N 2/006 600/14 |
| 2011/0065976 A1* | 3/2011 | Chornenky | A61N 1/40 600/14 |
| 2011/0112427 A1* | 5/2011 | Phillips | A61N 2/008 600/544 |
| 2013/0331907 A1 | 12/2013 | Sumners et al. | |
| 2014/0142669 A1* | 5/2014 | Cook | A61N 1/36146 607/116 |
| 2015/0360045 A1 | 12/2015 | Fischell et al. | |
| 2016/0045731 A1 | 2/2016 | Simon et al. | |

\* cited by examiner

HIGH FREQUENCY MAGNETIC FOOT STIMULATION

FIELD OF THE INVENTION

The present invention relates to devices and methods for treatment of a person's foot using high frequency magnetic pulse stimulation wherein the device is floor mounted and incorporates a cooling mechanism and heat sink.

BACKGROUND OF THE INVENTION

Foot pain can be caused by, for example, inflammation, bruising, fracture, or other irritation. For example, in plantar fasciitis, pain is associated with inflammation of the plantar fascia band. Foot pain can be a debilitating condition that negatively affects a person's quality of life.

A side effect of pain is often unwanted muscle contraction in the area as the body attempts to adjust to the pain, resulting in muscle spasticity. This tightening of the muscle in the area tends to exacerbate the situation, causing the pain to increase.

Peripheral magnetic stimulation (PMS) has been used to evaluate conduction times of peripheral nerves. Magnetic stimulation has advantages compared to electrical stimulation. Magnetic stimulation allows for deeper stimulation, inducing lower current densities through the skin where pain receptors are located. In general, the magnetic pulse frequency is low because high frequency pulses can result in heat buildup in the magnetic coil.

It has been shown that high frequency stimulation has an inhibitory effect on nerve communication, so direct stimulation of a muscle with high frequency stimulation would have a relaxing effect on a muscle and also have an anesthetic effect on nerve fibers in the stimulation area.

BRIEF SUMMARY

Described herein are methods and devices for treatment of a person's foot using high frequency magnetic pulse stimulation. Methods and devices described herein relax the muscles in the treatment region, and reduce the transmission of pain signals from the treatment region to the brain of the person.

In one aspect are devices that use magnetic pulses with a magnetic pulse frequency for treatment of a foot of a person comprising an enclosure, a treatment surface that is part of the enclosure, a magnetic pulse generator, a heat sink, and a cooling mechanism that cools the heat sink inside an enclosure. The enclosure can be, for example, floor- or cart-mounted. Preferably, the magnetic pulse generator is close to the treatment surface, configured to allow a person to place a foot against the treatment surface such that the sole of the foot is in close proximity to the magnetic pulse generator.

The heat sink removes heat from the magnetic pulse generator. It is therefore preferred to incorporate a mechanism that cools the heat sink. In some embodiments of at least one aspect described above, the cooling mechanism comprises a fan mounted to the enclosure wherein the fan causes airflow around the heat sink. The air is directed through the enclosure, and the intake and outlet ports are positioned to provide the best airflow possible around the heat sink. In some embodiments of at least one aspect described above, the cooling mechanism comprises liquid flowing around the heat sink. In some embodiments of at least one aspect described above, the cooling mechanism comprises a refrigeration unit. Types of refrigeration methods include non-cyclic, cyclic, thermoelectric, and magnetic. The preferred method for the present device is cyclic refrigeration, such as vapor-compression refrigeration used in the common heat pump.

In some embodiments of at least one aspect described above, the treatment surface is slanted at an angle to allow the person to be seated while placing a foot against the treatment surface. This allows the person to be seated comfortably, while placing one or both feet against the treatment surface. In some embodiments of at least one aspect described above, the treatment surface is approximately flat to allow the person to stand on the treatment surface.

It is very important for proper treatment that the person's foot be in the correct position so that magnetic pulses are delivered to the treatment region. In some embodiments of at least one aspect described above, the magnetic pulse generator location is adjustable to allow for different foot sizes or treatment regions. This also allows the treatment to be delivered to a specific treatment location without the person having to move the foot. In some embodiments of at least one aspect described above, the treatment surface comprises an indicator to the person of the proper placement of the foot. This indicator may be, for example, a dotted line that the person can see, which shows where their foot should be positioned. In some embodiments of at least one aspect described above, the treatment surface comprises a switch that will not allow magnetic pulses to be generated if the foot is not positioned correctly.

In order to induce relaxation of the muscle and a desensitization of the nerves that transmit pain signals to the brain, it is essential that the magnetic pulses be high frequency. In some embodiments of at least one aspect described above, the magnetic pulse frequency is from about 30 Hz to about 100 Hz. In some embodiments of at least one aspect described above, the magnetic pulse frequency is from about 100 Hz to about 500 Hz.

The magnetic pulse frequency may be fixed or variable, in order to best interface with intrinsic physiology. In some embodiments of at least one aspect described above, the magnetic pulse frequency is fixed at or near a target frequency. In some embodiments of at least one aspect described above, the magnetic pulse frequency hops periodically about an average target frequency. In some embodiments of at least one aspect described above, the magnetic pulse frequency hops periodically to random values within a range about an average target frequency. In some embodiments of at least one aspect described above, the magnetic pulse frequency hops periodically in a specific pattern about an average target frequency.

A higher energy magnetic field will generally provide increased benefits for the therapy. However, it is important that the magnetic pulses be comfortable for the person. In some embodiments of at least one aspect described above, the strength of the magnetic field is from about 10 Gauss to about 4 Tesla. In some embodiments of at least one aspect described above, the strength of the magnetic field pulses is adjusted based on the tolerance of the person.

In some embodiments of at least one aspect described above, the magnetic pulse generator is an electrical coil. The preferred embodiment is an electrical coil. However, the magnetic field generator could also comprise a moving permanent magnet, which creates a magnetic field by moving in a rotational, linear, or sway motion.

The device described herein is used for treatment of pain in the foot that results from a number of disorders. In some embodiments of at least one aspect described above, the treatment of the foot of the person alleviates the symptoms of plantar fasciitis, heel spur, stone bruise, heel fracture, metatarsalgia, Morton's neuroma, sesamoiditis, fallen arches, gout, bunion, hammertoe, claw toe, ingrown toenail, turf toe, toe sprain, toe fracture, hallux rigidus, corns, calluses, sesamoid fracture, neuropathy, and/or tendinitis. These symptoms may be, for example, pain and/or swelling.

BRIEF DESCRIPTION OF THE DRAWINGS

A better understanding of the features and advantages of the systems provided will be obtained by reference to the following detailed description that sets forth illustrative embodiments and the accompanying drawings of which.

DETAILED DESCRIPTION

Figure 1:
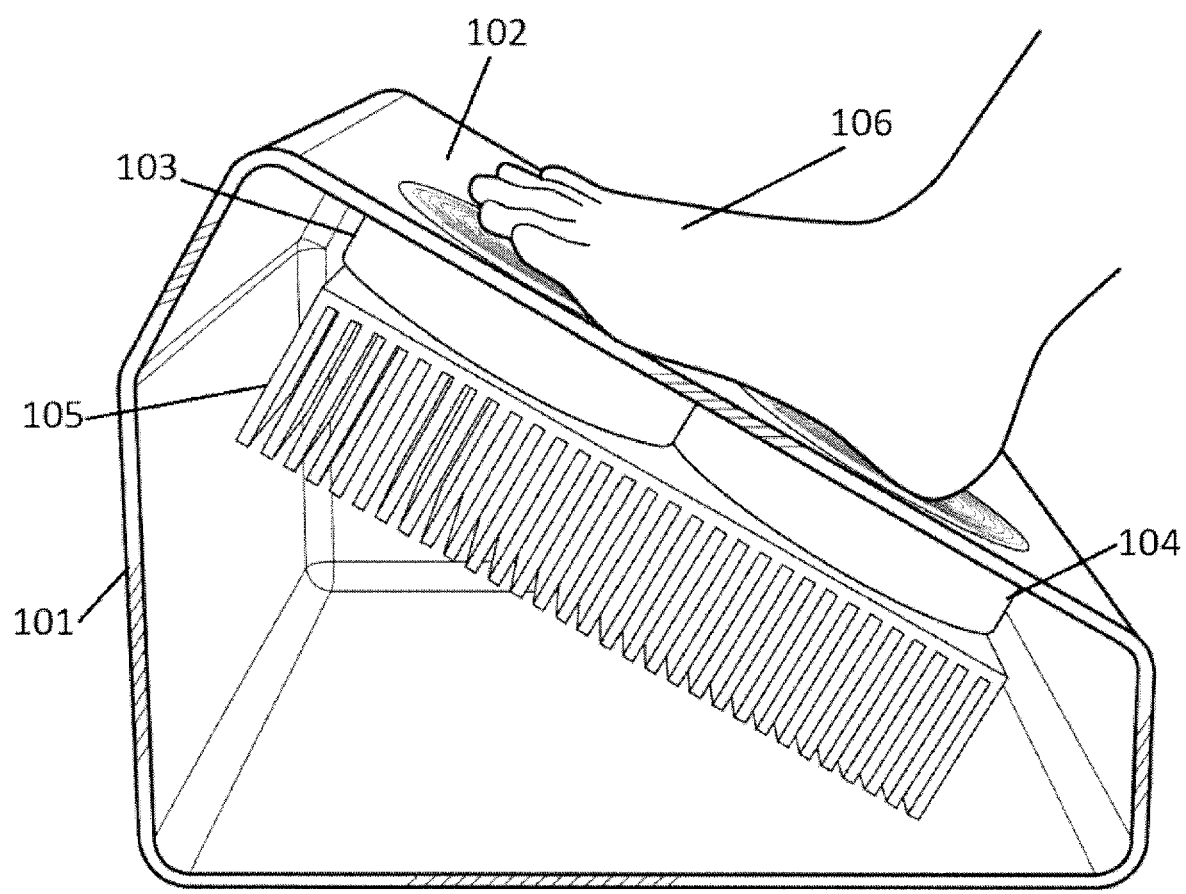
FIG. 1 shows an exemplary device in which two coils are mounted to a heat sink, showing coil location and foot placement.

While certain embodiments have been provided and described herein, it will be readily apparent to those skilled in the art that such embodiments are provided by way of example only. It should be understood that various alternatives to the embodiments described herein may be employed, and are part of the invention described herein.

Described herein are devices and methods for treatment of a person's foot using high frequency magnetic stimulation. By providing magnetic pulse stimulation at a high frequency to the sole of a person's foot, it is possible to relax the muscle in the treatment region, as well as reduce the communication of pain signals from the treatment region to the brain of the person.

The device incorporates one or more magnetic pulse generators in an enclosure that is preferably floor mounted. In order to keep the magnetic pulse generator cool and allow high frequency stimulation, a large heat sink is incorporated into the device in order to allow the heat from the magnetic pulse generator to be transferred to the heat sink. The magnetic field generator is configured so as to be close to a treatment surface, so that a person can position his/her foot close to the magnetic pulse generator.

The term "magnetic pulse generator" when referring to the device is the mechanism by which the magnetic field is produced. This is preferably an electric coil, but it could also be a moving permanent magnet. If the magnetic pulse generator is a coil, then an electric current pulse generator is required to create an electric current pulse in the coil, which generates a magnetic pulse through induction. The electric current pulse generator may connect to the device using a cable or connector, or the electric current pulse generator may be contained inside the enclosure.

The term "treatment region" when referring to the device is a region in or on the foot of a person where high frequency magnetic pulses are to be applied. The treatment region is chosen so that the pulses affect the symptoms for which treatment is being applied. For example, in treatment of plantar fasciitis, the pain is generally in the heel of the person, so the treatment region would be in or near the heel. More than one treatment region may exist in the person. For example, plantar fasciitis may also cause pain near the toes of the person. When multiple treatment regions exist, it may be required that the device incorporate more than one magnetic pulse generator so that treatment is applied to multiple treatment regions concurrently, or that treatment be applied using a single magnetic pulse generator to the multiple regions consecutively.

The term "treatment surface" when referring to the device is a surface that may or may not be part of the enclosure, and is configured to allow a person to place a foot against the treatment surface so that the sole of the foot is in the correct location to allow magnetic pulses to be applied to the treatment region. A treatment surface may cover multiple magnetic pulse generators, and there may be multiple treatment surfaces. For example, if a foot has multiple treatment regions, then a treatment surface may be configured to cover multiple magnetic pulse generators, allowing treatment of all treatment regions. Also, multiple treatment surfaces may exist to allow treatment of both feet without the need for the person to remove one foot and place the next foot on the treatment surface. Preferably the treatment surface is configured to allow the subject to place the sole of the foot against the treatment surface. However, the treatment surface could be configured so that another part of the foot is placed against the treatment surface. For example, the top of the foot or side of the foot may be placed against the treatment surface in order to affect one or more treatment regions.

The term "target frequency," when referring to the device, is the frequency of the magnetic pulses. When magnetic pulses are transmitted at a fixed frequency, the target frequency refers to this fixed value. When magnetic pulses are transmitted at a frequency that varies over time, either randomly or with a fixed pattern, the target frequency refers to the average of the magnetic pulse frequencies.

In one aspect are devices that use magnetic pulses with a magnetic pulse frequency for treatment of a foot of a person comprising an enclosure, a treatment surface that is part of the enclosure, a magnetic pulse generator, a heat sink, and a cooling mechanism that cools the heat sink inside an enclosure which is floor or cart mounted wherein the magnetic pulse generator is close to the treatment surface, configured to allow a person to place a foot against the treatment surface such that the sole of the foot is in close proximity to the magnetic pulse generator.

Preferably the device is floor mounted, because the heat sink can be large and heavy, and a floor mounted device is most easily adapted to allow a person to place a foot against the treatment surface. However, it is not absolutely required for the device to be floor mounted. Instead, the device could be mounted on, for example, a cart, which would allow the treatment surface to be positioned for people of varying stature. The device could also be mounted to an arm, which is moved into the correct position for treatment.

The purpose of the heat sink is to remove heat from the magnetic pulse generator. For example, at high frequency, the temperature of an electric coil tends to rise precipitously. In the present device, the coil is mounted so that the heat generated by the magnetic pulse generator is transferred to the heat sink, allowing high frequency magnetic pulses to be delivered for an extended period of time.

The heat sink may be a size and shape to allow it to fit easily in the enclosure, and to allow it to be cooled by a cooling mechanism. For example, the heat sink may incorporate a series of narrow fins to allow air or liquid to flow across as large a surface area as possible. Also, it is advantageous for the heat sink to be large, which allows for the greatest heat capacity. The material of the heat sink should have a high thermal conductivity, while being of a type that will not significantly alter the magnetic field generated by the coil. One example would be silicone. It may also be possible, also, for the coil to be liquid-cooled or gas-cooled, in which the liquid or gas surrounding the coil acts as a heat sink. If a liquid or gas heat sink is used, the liquid or gas is preferably outside the coil. Alternately, the coil could comprise a hollow tube, where the liquid or gas is forced to flow through the tube, in order to cool the coil.

The device incorporates a mechanism that cools the heat sink. In some embodiments of at least one aspect described above, the cooling mechanism comprises a fan mounted to the enclosure wherein the fan causes airflow around the heat sink. The air is directed through the enclosure, and the intake and outlet ports are positioned to provide the best airflow possible around the heat sink.

In some embodiments of at least one aspect described above, the cooling mechanism comprises liquid flowing around the heat sink. Liquid, such as water, has a higher thermal conductivity compared to air (0.6 vs 0.025 watts per meter per degree Kelvin). Therefore, water will tend to cool the heat sink much more quickly than air. As stated previously, if liquid or gas is used as the cooling mechanism, then the liquid or gas itself may act as the heat sink around the coil. However, water is more cumbersome to use than air because the enclosure would need to be sealed and a mechanism would be required to cycle the water through the enclosure and around the heat sink.

In some embodiments of at least one aspect described above, the cooling mechanism comprises a refrigeration unit. Types of refrigeration methods include non-cyclic, cyclic, thermoelectric, and magnetic. The preferred cooling method for the present device is cyclic refrigeration, such as vapor-compression refrigeration used in the common heat pump.

In some embodiments of at least one aspect described above, the treatment surface is slanted at an angle to allow the person to be seated while placing a foot against the treatment surface. This allows the person to be seated comfortably, while placing one or both feet against the treatment surface. An optional leg-rest may be used to reduce any variation in pressure of the foot against the treatment surface, and to maximize comfort for the person. In some embodiments of at least one aspect described above, the treatment surface is approximately flat to allow the person to stand on the treatment surface. This allows for significant pressure to be placed on the sole of the foot, minimizing separation of the foot with the magnetic pulse generator, and maximizing the strength of magnetic pulses delivered to the foot.

In some embodiments of at least one aspect described above, the magnetic pulse generator location is adjustable to allow for different foot sizes or treatment regions. For example, if the treatment location is on the heel of the person but the magnetic pulse generator is positioned near his/her toes, the magnetic pulse generator location could be adjusted so that it is positioned under the heel. This improves usability of the device, so that the person is not required to shift his/her foot to a different position on the treatment surface to apply magnetic pulses to a different treatment region. Having an adjustable magnetic pulse generator would make it possible to easily apply magnetic pulses to any treatment region without having the person adjust his/her foot or requiring multiple magnetic field generators.

In some embodiments of at least one aspect described above, the treatment surface comprises an indicator to the person of the proper placement of the foot. This indicator may be a dotted line that the person can see, which shows where his/her foot should be positioned. It may also be a dotted line showing the location of the maximum magnetic field, based on the location of the magnetic pulse generator relative to the treatment surface.

In some embodiments of at least one aspect described above, the treatment surface comprises a switch that will not allow magnetic pulses to be generated if the foot is not positioned correctly. This switch may comprise a pressure-plate or capacitive switch near the magnetic field generator, which detects when the foot is being pressed against the treatment surface. It may also comprise a photo-diode, which will indicate whether or not the foot is in position.

In order to induce relaxation of the muscle and a desensitization of the nerves that transmit pain signals to the brain, it is essential that the magnetic pulses be high frequency. In some embodiments of at least one aspect described above, the magnetic pulse frequency is from about 30 Hz to about 100 Hz. In some embodiments of at least one aspect described above, the magnetic pulse frequency is from about 100 Hz to about 500 Hz. Although the magnetic pulse frequency could exceed 500 Hz, the effect would be reduced, since neurons cannot process signals at that high a frequency. Also, the heat generated by the magnetic pulse generator would be prohibitive.

Preferably, the magnetic pulses are generated at a specified fixed frequency, although it is possible to vary the frequency of magnetic pulses about a specific target frequency. By adjusting the stimulus frequency over time, one may interface more effectively with intrinsic physiology. The variation of pulse frequency may be in a specific pattern or random. In some embodiments of at least one aspect described above, the magnetic pulse frequency is fixed at or near a target frequency. In some embodiments of at least one aspect described above, the magnetic pulse frequency hops periodically about an average target frequency. In some embodiments of at least one aspect described above, the magnetic pulse frequency hops periodically to random values within a range about an average target frequency. In some embodiments of at least one aspect described above, the magnetic pulse frequency hops periodically in a specific pattern about an average target frequency. The pattern or range of frequency hopping could also be part of the optimization algorithm. For example, if Gaussian distributed random frequency hopping was used, then the algorithm could maximize settling time over both pulse frequency and standard deviation of the magnetic pulses.

In some embodiments of at least one aspect described above, the strength of the magnetic field is from about 10 Gauss to about 4 Tesla. Although higher energy pulses would tend to have a more significant effect, entrainment in the neurons may not require the energy to be extremely high. Very high energy pulses may be painful for the person, making the treatment uncomfortable and making it difficult for the person to keep his/her foot in the correct position. In some embodiments of at least one aspect described above, the strength of the magnetic field pulses is adjusted based on the tolerance of the person. For example, a dial could allow for adjustment of magnetic field strength, and the person could set the magnetic field strength as high as possible without being painful.

In some embodiments of at least one aspect described above, the magnetic pulse generator is an electrical coil. The preferred embodiment is an electrical coil. However, the magnetic field generator could also comprise a moving permanent magnet, which creates a magnetic field by moving in a rotational, linear, or sway motion. However, a moving permanent magnet would not easily create a high enough energy pulse to be effective.

The device described herein is used for treatment of pain in the foot that results from a number of disorders. The specific disorder is not a factor in treatment, other than to assist in finding the optimal target region. In some embodiments of at least one aspect described above, the treatment of the foot of the person alleviates the symptoms of plantar fasciitis, heel spur, stone bruise, heel fracture, metatarsalgia, Morton's neuroma, sesamoiditis, fallen arches, gout, bunion, hammertoe, claw toe, ingrown toenail, turf toe, toe sprain, toe fracture, hallux rigidus, corns, calluses, sesamoid fracture, neuropathy, or tendinitis.

FIG. 1 shows an exemplary device, in which the side of the enclosure (101) has been removed to show two coil-type magnetic pulse generators (103, 104) mounted to a large heat sink (105). In this example, is intended that air or fluid flows through the fins of the heat sink to cool it. The person's foot (106) is placed on the treatment surface (102), which has been removed in this example, in order to display the coils' position under the foot.

Figure 2:
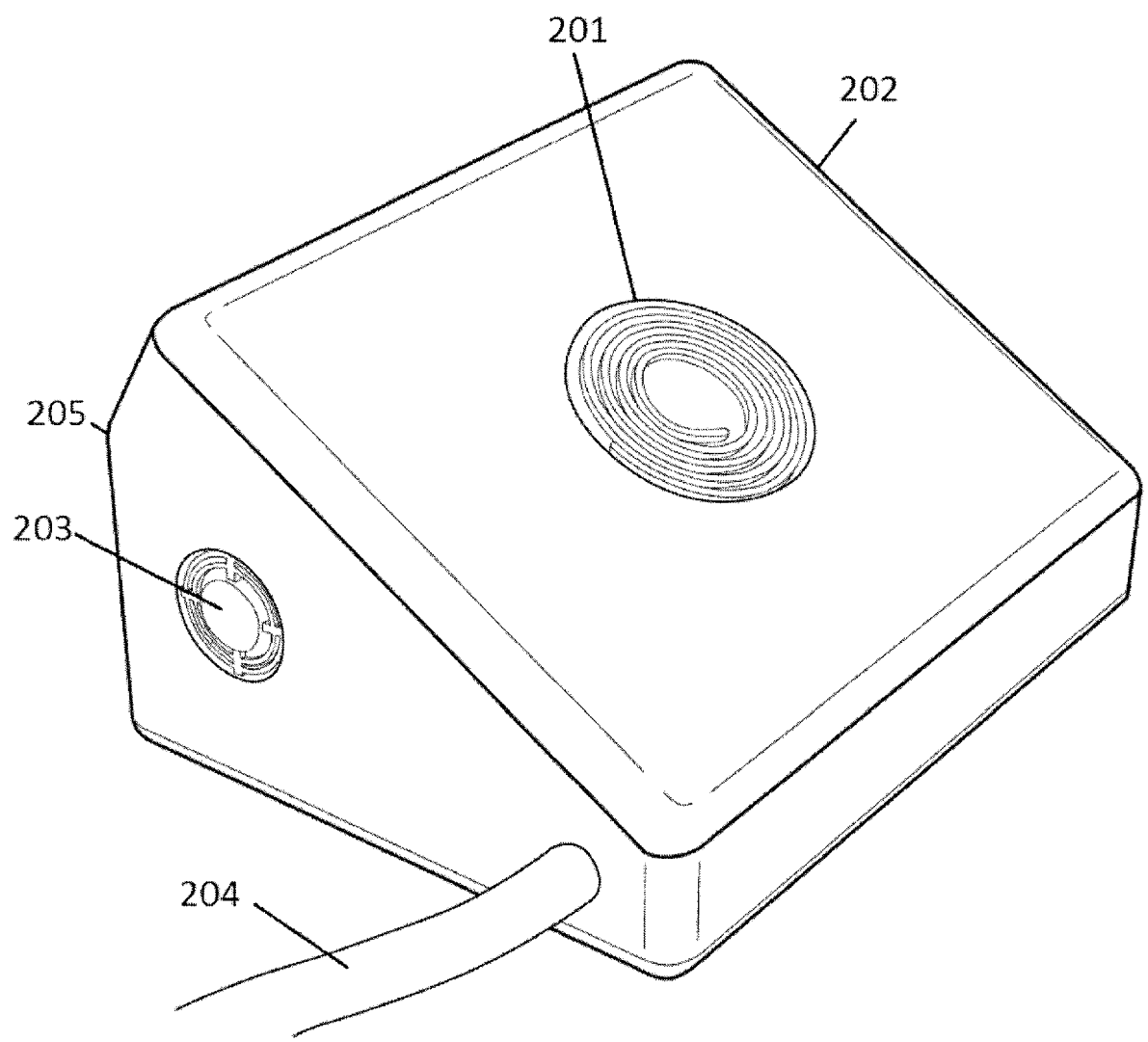
FIG. 2 shows an exemplary device in which a single coil is positioned beneath the treatment surface.

FIG. 2 shows an exemplary device, in which a single coil (201) is situated in the center of the enclosure (205). In this example, the treatment surface (202) has been removed to show the position of the coil. A fan (203) is placed to blow air across the fins of the heat sink. A cable (204) goes from the coil to an electric current pulse generator.

Figure 3:
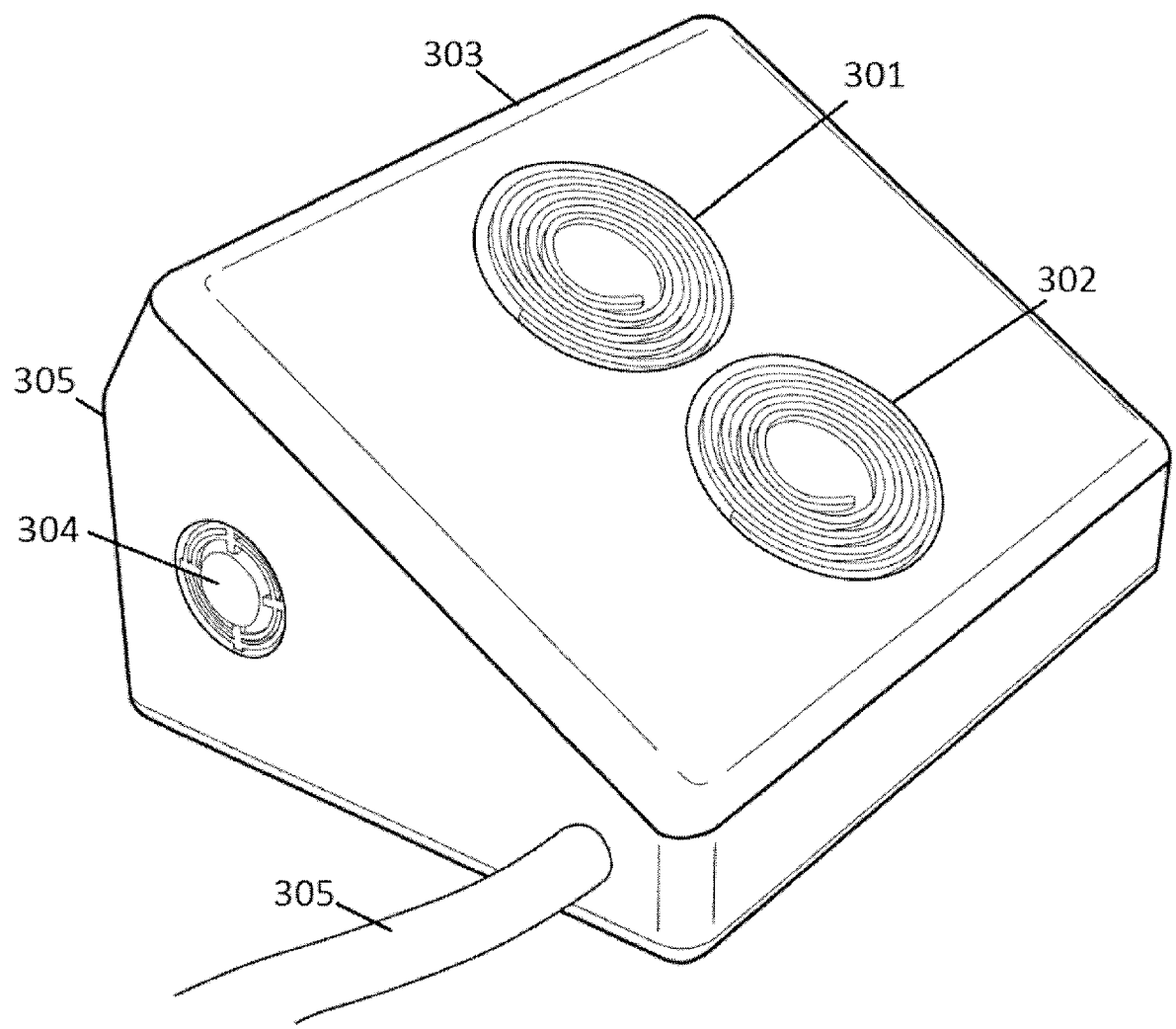
FIG. 3 shows an exemplary device in which two coils are positioned beneath the treatment surface, in order to provide magnetic pulses to two locations on the foot.

FIG. 3 shows an exemplary device, in which two coils (301, 302) are situated in the center of the enclosure (305). This allows magnetic pulses to be delivered to two portions of a person's foot concurrently or alternating between the two. In this example, the treatment surface (303) has been removed to show the position of the coils. A fan (304) is placed to blow air across the fins of the heat sink. A cable (305) goes from the coil to an electric current pulse generator.

Figure 4:
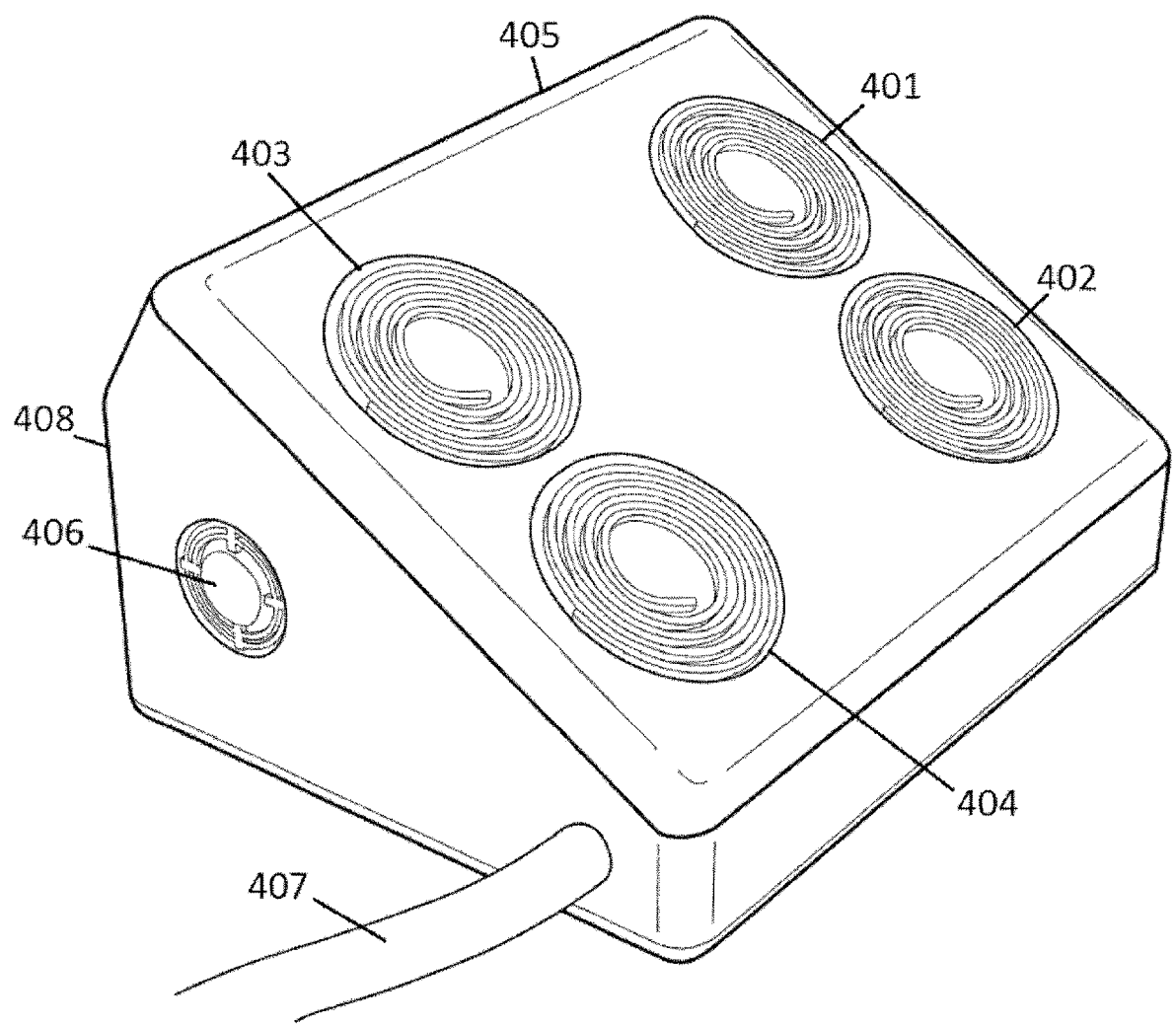
FIG. 4 shows an exemplary device in which four coils are positioned beneath the treatment surface, to allow magnetic pulses to be provided to two locations on both feet of the person.

FIG. 4 shows an exemplary device, in which four coils (401, 402, 403, 404) are situated in the enclosure (408). This allows magnetic pulses to be delivered to two portions of both of a person's feet concurrently or alternating. In this example, the treatment surface (405) has been removed to show the position of the coils. A fan (406) is placed to blow air across the fins of the heat sink. A cable (407) goes from the coil to an electric current pulse generator.

Figure 5:
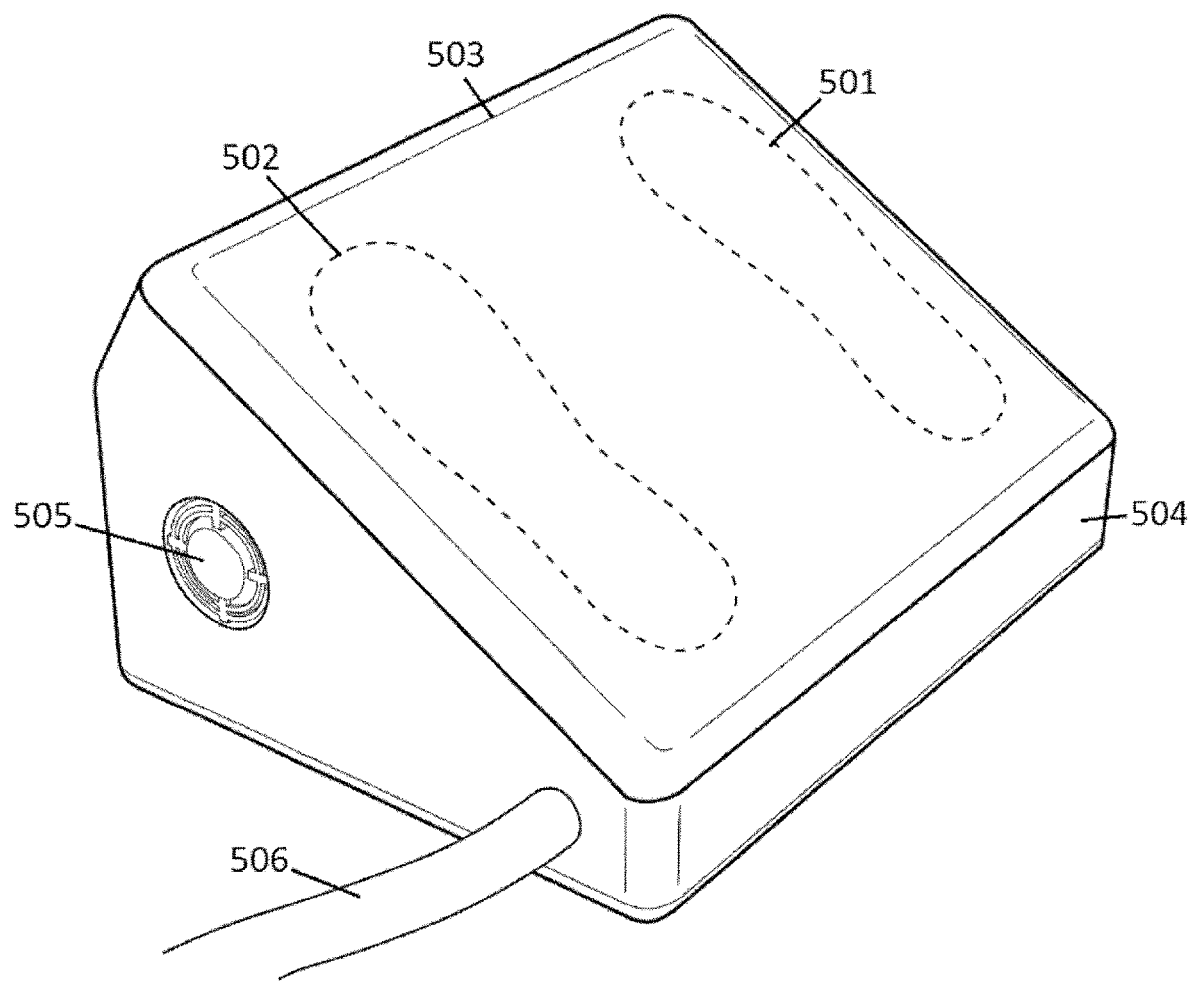
FIG. 5 shows an exemplary device in which a dotted line indicator on the treatment surface shows where the person should placefoot.

FIG. 5 shows an exemplary device, in which dotted lines (501, 502) are indicators showing where the person should place their feet to ensure optimal coil placement. The indicators are on the treatment surface (503), which is part of the enclosure (504). A fan (505) is placed to blow air across the fins of the heat sink. A cable (506) goes from the coil to an electric current pulse generator.

Figure 6:
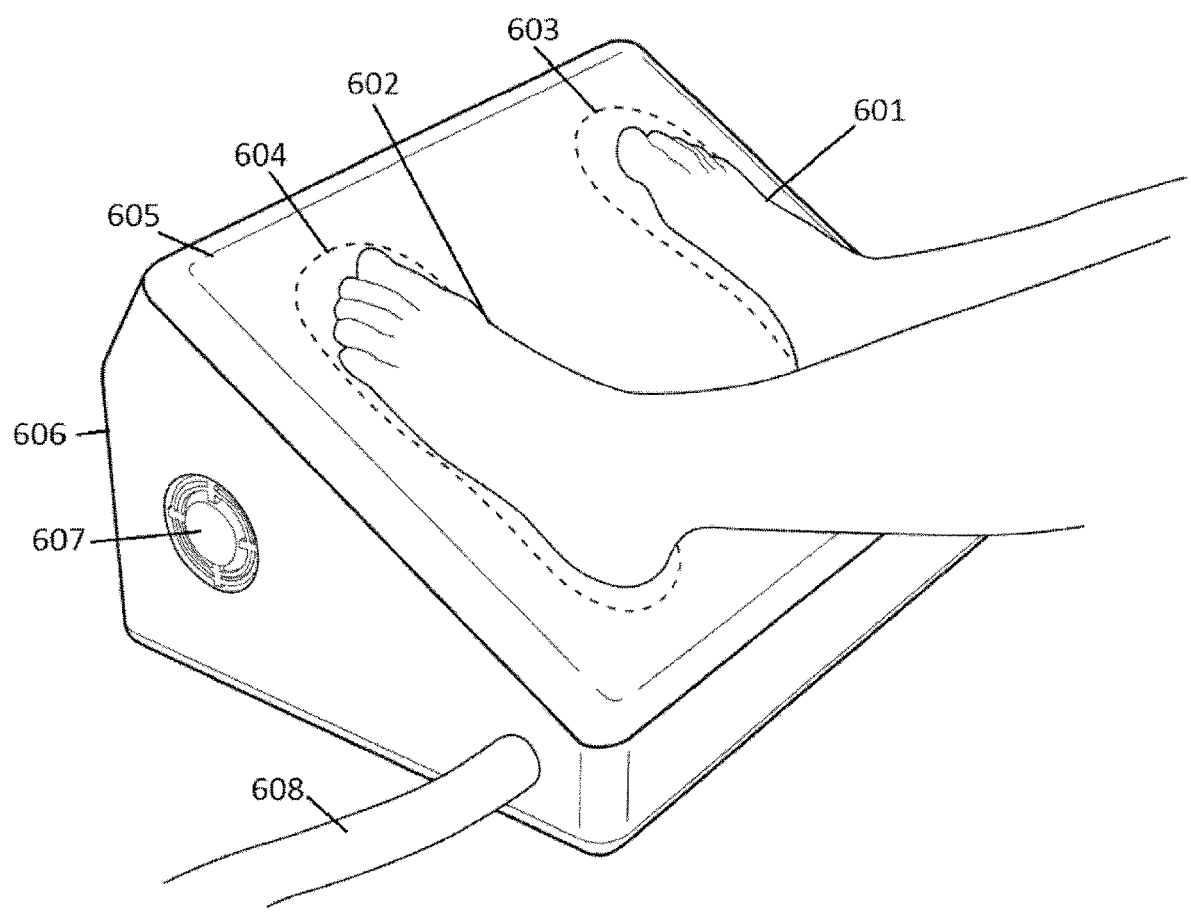
FIG. 6 shows an exemplary device where the person's feet are placed in the correct position according to the dotted line indicator on the treatment surface.

FIG. 6 shows an exemplary device, in which the person's feet (601, 602) are placed correctly in accordance with the dotted line indicators (603, 604). The indicators are on the treatment surface (605), which is part of the enclosure (606). A fan (607) is placed to blow air across the fins of the heat sink. A cable (608) goes from the coil to an electric current pulse generator.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the devices are not intended to be exhaustive or to be limited to the precise form disclosed. While specific embodiments of, and examples for, the devices are described herein for illustrative purposes, various equivalent modifications are possible within the scope of the devices, as those skilled in the relevant art will recognize. The teachings of the methods, or devices provided herein can be applied to other processing devices, not only for the devices described.

The elements and acts of the various embodiments described can be combined to provide further embodiments. These and other changes can be made to the device in light of the above detailed description.

In general, in the following claims, the terms used should not be construed to limit the devices to the specific embodiments disclosed in the specification and the claims, but should be construed to include all processing devices that operate under the claims. Accordingly, the methods and devices are not limited by the disclosure, but instead the scopes of the devices are to be determined entirely by the claims.

While certain aspects of the devices are presented below in certain claim forms, the inventor contemplates the various aspects of the devices in any number of claim forms. Accordingly, the inventors reserve the right to add additional claims after filing the application to pursue such additional claim forms for other aspects of the devices.

EMBODIMENTS

Specific embodiments of the invention include the following:

1. A device that uses magnetic pulses having a magnetic pulse frequency for treatment of a foot of a person comprising an enclosure, a treatment surface that is part of the enclosure, a magnetic pulse generator, a heat sink, and a cooling mechanism that cools the heat sink inside an enclosure that is floor or cart mounted wherein the magnetic pulse generator is close to the treatment surface, configured to allow a person to place a foot against the treatment surface such that the sole of the foot is in close proximity to the magnetic pulse generator.
2. The device of Embodiment 1 wherein the cooling mechanism comprises a fan mounted to the enclosure wherein the fan causes airflow around the heat sink.
3. The device of Embodiment 1 wherein the cooling mechanism comprises liquid flowing around the heat sink.
4. The device of Embodiment 1 wherein the cooling mechanism comprises a refrigeration unit.
5. The device of Embodiment 1 wherein the treatment surface is slanted at an angle to allow the person to be seated while placing a foot against the treatment surface.

6. The device of Embodiment 1 wherein the treatment surface is approximately flat to allow the person to stand on the treatment surface.
7. The device of Embodiment 1 wherein the magnetic pulse generator location is adjustable to allow for different foot sizes or treatment location.
8. The device of Embodiment 1 wherein the treatment surface comprises an indicator to the person of the proper placement of the foot.
9. The device of Embodiment 1 wherein the treatment surface comprises a switch that will not allow magnetic pulses to be generated if the foot is not positioned correctly.
10. The device of Embodiment 1 wherein the magnetic pulse frequency is from about 30 Hz to about 100 Hz.
11. A device of Embodiment 1 wherein the magnetic pulse frequency is from about 100 Hz to about 500 Hz.
12. The device of Embodiment 1 wherein the magnetic pulse frequency is fixed at or near a target frequency.
13. The device of Embodiment 1 wherein the magnetic pulse frequency hops periodically about an average target frequency.
14. The device of Embodiment 13 wherein the magnetic pulse frequency hops periodically to random values within a range about an average target frequency.
15. The device of Embodiment 13 wherein the magnetic pulse frequency hops periodically in a specific pattern about an average target frequency.
16. The device of Embodiment 1 wherein the strength of the magnetic field pulses is from about 10 Gauss to about 4 Tesla.
17. The device of Embodiment 1 wherein the strength of the magnetic field pulses is adjusted based on the tolerance of the person.
18. The device of Embodiment 1 wherein the magnetic pulse generator is an electrical coil.
19. The device of Embodiment 1 wherein the treatment of the foot of the person alleviates the symptoms of plantar fasciitis, heel spur, stone bruise, heel fracture, metatarsalgia, Morton's neuroma, sesamoiditis, fallen arches, gout, bunion, hammertoe, claw toe, ingrown toenail, turf toe, toe sprain, toe fracture, hallux rigidus, corns, calluses, sesamoid fracture, neuropathy, and/or tendinitis.
20. A method for the treatment of a foot condition, wherein said method comprises applying magnetic stimulation, using a device of Embodiment 1, to a foot in need of such treatment.
21. The method of Embodiment 19 used to treat the symptoms of plantar fasciitis, heel spur, stone bruise, heel fracture, metatarsalgia, Morton's neuroma, sesamoiditis, fallen arches, gout, bunion, hammertoe, claw toe, ingrown toenail, turf toe, toe sprain, toe fracture, hallux rigidus, corns, calluses, sesamoid fracture, neuropathy, and/or tendinitis.

We claim:
1. A device that uses magnetic pulses having a variable magnetic pulse frequency for treatment of a foot of a person, the device comprising:
   an enclosure having a treatment surface,
   a magnetic pulse generator comprising a planar spiral coil coplanar with the treatment surface within the enclosure,
   an electric current pulse generator configured to create an electric current pulse in the magnetic pulse generator, which generates magnetic pulses through induction,
   wherein the device is configured to have the magnetic pulse frequency hop during treatment, periodically about an average target frequency,
   wherein the device is configured to shift the magnetic pulse frequency, during treatment, periodically to random values within a range that spans from 30 Hz to 500 Hz; and
   wherein the treatment surface comprises a switch that allows magnetic pulses to be generated when the foot is positioned correctly, and an indicator that indicates that the foot is positioned correctly.
2. The device of claim 1, wherein the treatment surface is part of the enclosure and the magnetic pulse generator is close to the treatment surface.
3. The device of claim 2, wherein the magnetic pulse generator and treatment surface are positioned to allow the foot to be placed against the treatment surface such that a sole of the foot is in close proximity to the magnetic pulse generator.
4. The device of claim 3, wherein the treatment surface is slanted at an angle to allow the person to be seated while placing the foot against the treatment surface.
5. The device of claim 3, wherein the treatment surface has no slope.
6. The device of claim 3, wherein the magnetic pulse generator location is adjustable to allow for different foot sizes or treatment locations.
7. The device of claim 3, further comprising a heat sink comprising one or more fins, and a cooling mechanism that cools the heat sink inside the enclosure.
8. The device of claim 1, wherein a respective strength of each magnetic field pulse is adjusted based on a tolerance of the person.
9. A method for treatment of a foot of a person, wherein the method comprises:
   placing the foot of the person on a treatment surface;
   generating an electric current pulse to generate a variable magnetic pulse through induction using a planar spiral coil coplanar with the treatment surface, the magnetic pulse having a variable magnetic pulse frequency;
   activating a switch by positioning the foot on an indicator that indicates that the foot is positioned properly on the treatment surface;
   applying the magnetic pulse to the foot in response to activation of the switch; and
   hopping the magnetic pulse frequency of the applied variable magnetic pulse during treatment periodically about an average target frequency,
   wherein the magnetic pulse frequency shifts during treatment periodically to random values within a range that spans from 30 Hz to 500 Hz.
10. The method of claim 9, wherein the method further comprises shifting the magnetic pulse frequency, during treatment, periodically to random values in a non-incremental manner.
11. A method for treatment of a foot of a person, wherein the method comprises:
   placing the foot of the person on a treatment surface;
   generating an electric current pulse to generate a variable magnetic pulse through induction using a planar spiral coil coplanar with the treatment surface, the magnetic pulse having a variable magnetic pulse frequency;
   activating a switch by positioning the foot on an indicator that indicates that the foot is positioned properly on the treatment surface;
   applying the magnetic pulse to the foot in response to activation of the switch;

hopping the magnetic pulse frequency of the applied variable magnetic pulse during treatment periodically about an average target frequency;

wherein the magnetic pulse frequency shifts during treatment periodically to random values within a range that spans from 30 Hz to 500 Hz; and inducing relaxation of a muscle of the foot of the person and desensitization of a nerve that transmits pain signals to the brain of the subject.

12. The method of claim 11, wherein the method further comprises shifting the magnetic pulse frequency, during treatment, periodically to random values in a non-incremental manner.

* * * * *